(12) United States Patent
Ashizuka et al.

(10) Patent No.: US 11,986,151 B2
(45) Date of Patent: May 21, 2024

(54) ENDOSCOPE AND OPTICAL PROBE SYSTEMS

(71) Applicant: OLYMPUS MEDICAL SYSTEMS CORP., Tokyo (JP)

(72) Inventors: Masahiro Ashizuka, Hino (JP); Sergey A. Bukesov, Acton, MA (US); Kester J. Batchelor, Mound, MN (US)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 17/843,821

(22) Filed: Jun. 17, 2022

(65) Prior Publication Data
US 2022/0409021 A1   Dec. 29, 2022

Related U.S. Application Data

(60) Provisional application No. 63/300,480, filed on Jan. 18, 2022, provisional application No. 63/216,019, filed on Jun. 29, 2021.

(51) Int. Cl.
*A61B 1/00* (2006.01)
*A61B 1/05* (2006.01)
(Continued)

(52) U.S. Cl.
CPC .......... *A61B 1/00096* (2013.01); *A61B 1/05* (2013.01); *A61B 1/07* (2013.01); *G02B 23/2469* (2013.01); *A61B 1/00165* (2013.01)

(58) Field of Classification Search
CPC .......... A61B 1/00071; A61B 1/00096; A61B 1/00098; A61B 1/00165; A61B 1/005; A61B 1/0051; A61B 1/018; A61B 1/07
(Continued)

(56) References Cited

U.S. PATENT DOCUMENTS 5,379,779 A * 1/1995 Rowland ............... A61M 25/09
604/528
6,451,005 B1 * 9/2002 Saitou ............... A61M 25/0053
604/526
(Continued)

FOREIGN PATENT DOCUMENTS

JP    S56-119263 A       9/1981
JP    H02-118505    *    9/1990
(Continued)

*Primary Examiner* — Timothy J Neal
*Assistant Examiner* — James Edward Boice
(74) *Attorney, Agent, or Firm* — Morgan, Lewis & Bockius LLP

(57) ABSTRACT

The endoscope has an insertion portion, an imaging unit, and a member formed in a given dimension. The insertion portion has an apical portion, an actively curvable portion, and a treatment device channel. The actively curvable portion is located on the proximal side of the apical portion. The treatment device channel is positioned along the longitudinal axis of the insertion portion. The insertion portion is formed of resin. One or more radiopaque members, formed of knowns dimensions, are coated on a surface of the insertion portion or placed in, buried or covered laterally in the insertion portion. The X-ray transmittance of the radiopaque members is different from the X-ray transmittance of the resin forming the insertion portion.

13 Claims, 13 Drawing Sheets

(51) Int. Cl.
*A61B 1/07* (2006.01)
*G02B 23/24* (2006.01)

(58) Field of Classification Search
USPC .......................................... 600/109
See application file for complete search history.

(56) References Cited

U.S. PATENT DOCUMENTS

| | | | | |
|---|---|---|---|---|
| 2004/0049095 A1* | 3/2004 | Goto | ................. | A61B 1/00098 |
| | | | | 600/107 |
| 2009/0281376 A1* | 11/2009 | Acosta | ................. | A61F 5/0003 |
| | | | | 600/114 |
| 2020/0237969 A1* | 7/2020 | Kuroda | ............. | A61M 25/0045 |

FOREIGN PATENT DOCUMENTS

| | | | | |
|---|---|---|---|---|
| JP | H02-118505 U | | 9/1990 | |
| JP | 2948615 B2 | | 9/1999 | |
| JP | 2002172173 A | * | 6/2002 | |
| WO | WO-2006016481 A1 | * | 2/2006 | ............ A61M 25/00 |

\* cited by examiner

ENDOSCOPE AND OPTICAL PROBE SYSTEMS

RELATED APPLICATION DATA

This application is based on and claims priority under 35 U.S.C. § 119 to U.S. Provisional Application No. 63/216,019 filed on Jun. 29, 2021, and to U.S. Provisional Application No. 63/300,480 filed on Jan. 18, 2022, the entire contents of each of these applications are incorporated herein by reference.

FIELD OF THE INVENTION

The present invention relates to an endoscope and an optical probe system capable of evaluating the size of a portion to be measured.

DESCRIPTION OF THE RELATED ART

Traditionally, stones such as gallstones in the body are fragmented by laser light from laser probes, etc., and then removed from the body cavity. When performing such actions, there is a demand to evaluate the diameter of the stones and the length of the stricture. Traditionally, the size of stones and strictures has been assessed under radiographic observation, for example by comparing the stone to the thickness of the inserted endoscope (e.g., about 10 mm).

Japanese Patent No. 2948615 B2 discloses a prior art embodiment having a resin tube with radiopaque paint applied to the outer surface, which can be used as a heat shrinking tube that covers pipes made of radiopaque material.

SUMMARY OF THE INVENTION

An endoscope according to an aspect of the present invention includes an insertion portion having a tip configuration with an apical portion, a portion that is configured to be curved, for example, by manipulation by a user (also called herein an actively curvable portion), and a lumen. The actively curvable portion is positioned at the base of the apical portion. The lumen is positioned along the longitudinal axis of the insertion portion. The insertion portion is formed by resin. An imaging unit is located in the insertion portion, such as in a lumen. A member having a predetermined dimension is placed in the lumen, or is coated on a surface of the insertion portion, or is buried or covered laterally in the insertion portion, and the radiolucency of the member differs from that of the resin.

The optical probe system according to one aspect of the invention comprises a light source emitting a first light, a light probe with first and second light guides, where the first light guide transmits the first light and directs the first light to irradiate a part of measured object and the second light guide receives and transmits the second light, which is the return light from the measured object, a sensor measuring the brightness of the second light, and an analyzer that calculates the size of the measured object based on the brightness of the second light measured by the sensor.

DETAILED DESCRIPTION OF THE PREFERRED EMBODIMENT(S)

Figure 1:
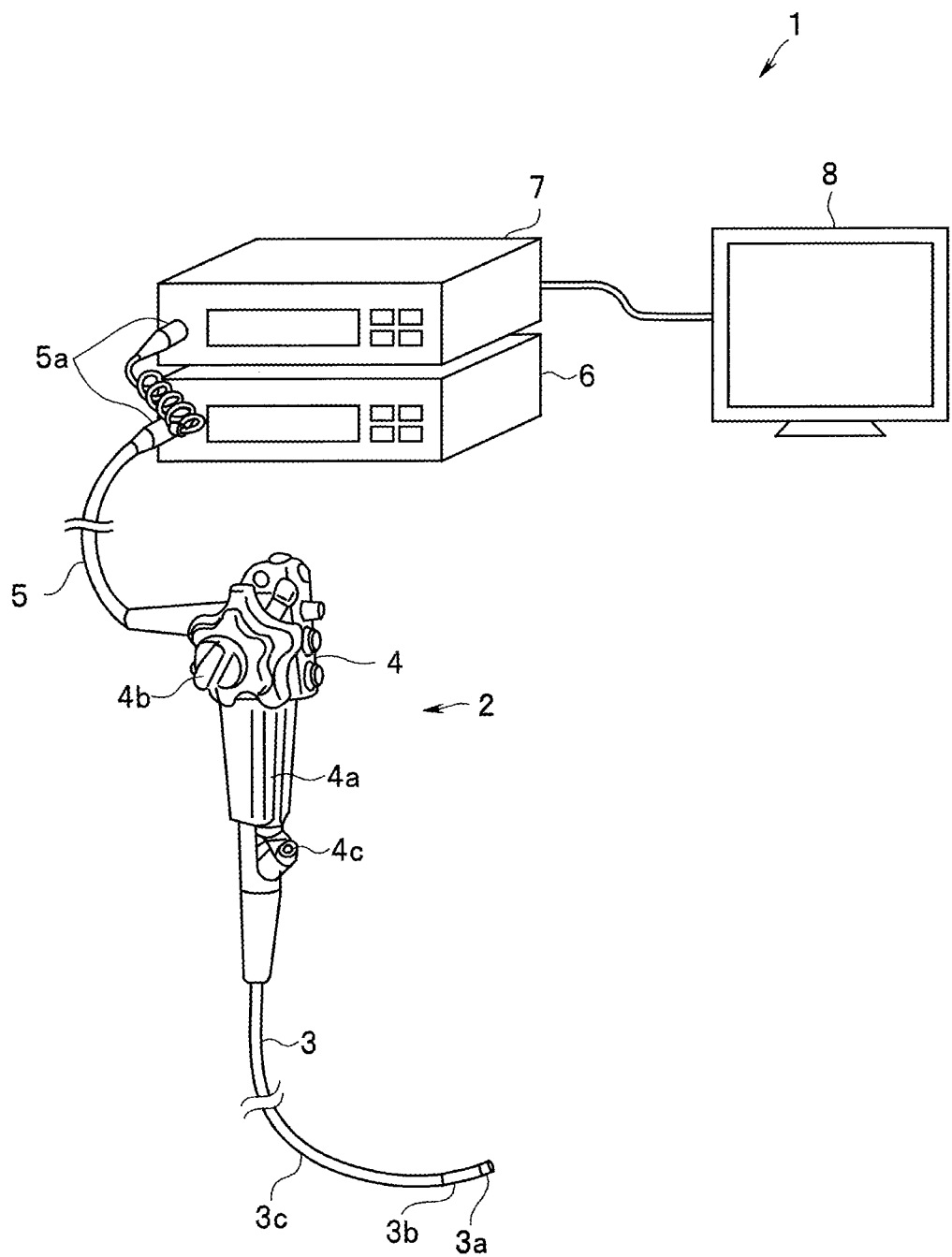
FIG. 1 is a diagram showing an endoscope system of a first embodiment of the present invention.

According to disclosed embodiments, it is possible to provide an endoscope and an optical probe system capable of evaluating the size of the measurement target portion.

The disclosures herein generally apply to endoscopes, including reusable endoscopes, which are used multiple times by performing recycling or refurbishment processing, and single-use endoscopes, which are used only once. Compared with reusable endoscopy, single-use endoscopy is difficult to use the thickness of the insertion site to assess the size of the measured area, as is the case with reusable endoscopy, because more resin material is used to penetrate the X-ray.

Embodiments of the invention are hereafter illustrated with reference to the drawings. However, the present invention is not limited by the embodiments described below. In the drawings, the same or corresponding elements are signed as appropriate. It should also be noted that the drawings are schematic and that the length relationship of each element, the ratio of the length of each element, and the number of each element within a single drawing may differ from the reality for clarity. In addition, there may be parts that differ in their length relationships and ratios between each other in multiple views.

First Embodiment

FIGS. 1 to 10 show a first embodiment of the present invention, and FIG. 1 is a diagram illustrating an endoscope system.

As shown in FIG. 1, the endoscope system 1 includes an endoscope 2, a light source device 6, an endoscope control device 7, and a monitor 8. Endoscope 2 is equipped with insertion portion 3, operation unit 4, and universal cable 5. Insertion portion 3 is an elongated tube inserted into the body cavity of the subject. The subject in which the insertion portion 3 is inserted can be a human body, as an example, but is not limited to the human body and may be an organism, such as an animal, or may be an abiotic object, such as a machine or a building. Insertion portion 3 includes an apical portion 3a, an actively curvable portion 3b, and a flexible tube portion 3c, in order from the distal tip end to the proximal base end.

Figure 2:
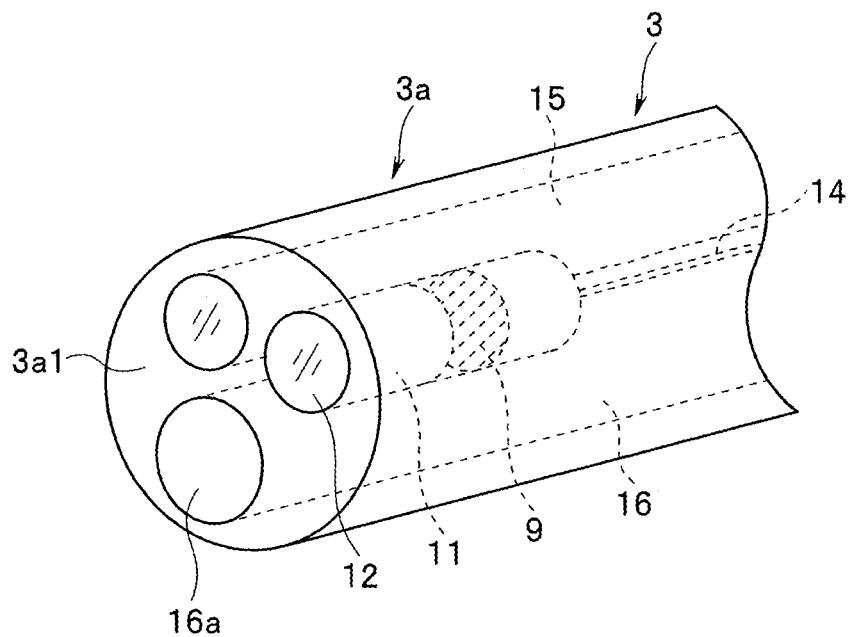
FIG. 2 is a perspective view showing a distal end configuration portion of the endoscope of the first embodiment described above.
Figure 3:
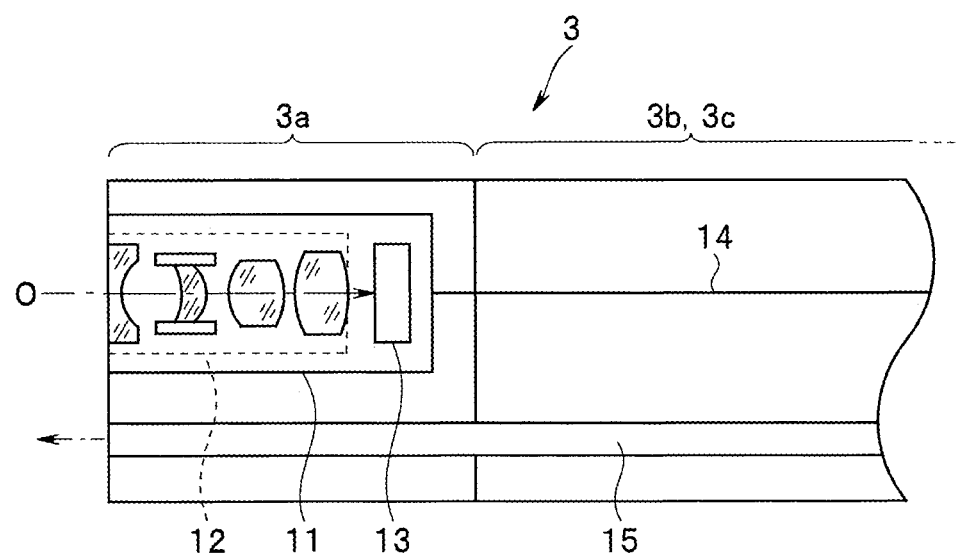
FIG. 3 is a diagram showing an internal configuration of a distal end configuration portion of the endoscope of the first embodiment described above.

Endoscope 2 is constructed as an electronic endoscope and, as shown in FIGS. 2 and 3, in the lumen within the apical portion 3a there is an imaging unit 11 for imaging a subject. FIG. 2 is a perspective view showing the apical portion 3a of endoscope 2, and FIG. 3 shows some of the internal features of the apical portion 3a of endoscope 2.

As shown in FIG. 3, the imaging unit 11 includes an objective optical system 12 in which a plurality of lenses is arranged along the optical axis O, and an imaging element 13 for outputting an electric signal by photoelectrically converting an optical image imaged by the objective optical system 12. Other features inside the insertion portion 3 include a signal line 14 is connected to the imaging element 13, a light guide 15 transmitting illumination light, a treatment device channel 16 for intubating the endoscopic treatment device, etc. The tip of the light guide 15 for irradiating the transmitted illumination light toward the subject, the distal end lens of the objective optical system 12, and the distal end opening 16a of the treatment device channel 16 are arranged on the distal end surface 3a1 of the apical portion 3a.

Figure 4:
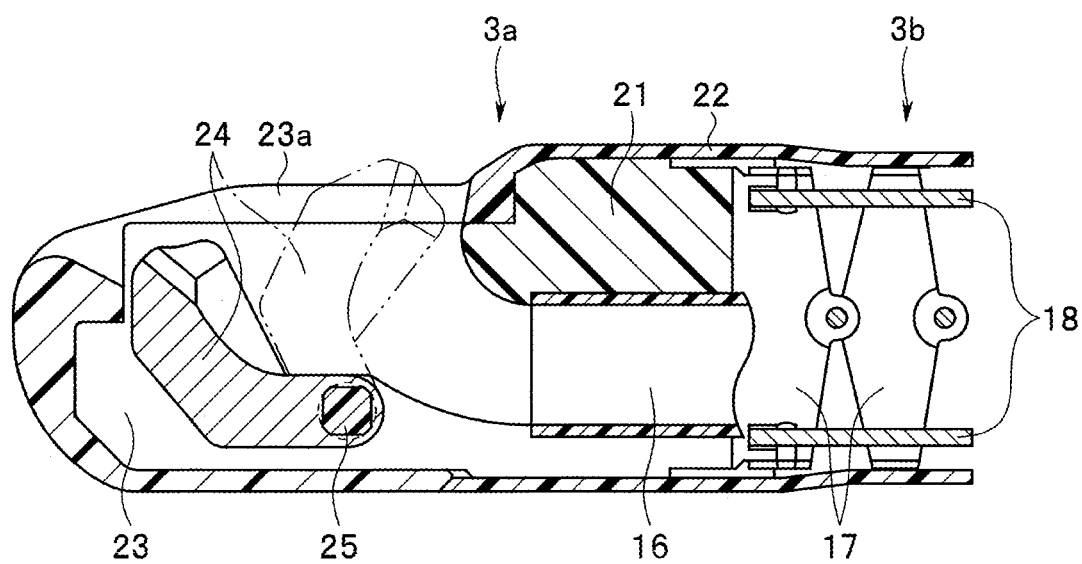
FIG. 4 shows, for the first embodiment above, a cross-sectional view showing a configuration example in which an arm was placed in the tip configuration of the endoscope to change the direction of the procedural device protruding from the treatment device channel.

Actively curvable portion 3b is a bendable portion positioned at the base-end of the apical portion 3a. Actively curvable portion 3b is, for example, configured to be curved in two directions or is configured to be curved in four directions of the vertical and horizontal directions. As shown in FIG. 4, in the actively curvable portion 3b a plurality of curved frames 17 are pivotably connected along the longitudinal axis of the insertion portion 3. A distal end of a wire 18 is connected to the curved frame 17 in the insertion portion 3 and a proximal end of the wire 18 is connected to a bending operation knob 4b of the operation unit 4. When the actively curvable portion 3b is curved by manipulation of the wire 18, the direction of the apical portion 3a is changed and the observation direction of the imaging unit 11 and the irradiation direction of the illumination light from the light guide 15 are changed. The actively curvable portion 3b can also be curved to improve insertability within the subject.

The flexible tube portion 3c is positioned at the base-end side of the actively curvable portion 3b.

The operation unit 4 is disposed on the proximal end side of the insertion portion 3 and includes a gripping portion 4a, a bending operation knob 4b, and a treatment device insertion port 4c. The gripping portion 4a is the site where the operator holds the endoscope 2 by the palm during operation. The bending operation knob 4b is a device, such as a knob or lever, for performing the operation of bending the actively curvable portion 3b using, for example, a thumb of a hand that holds the gripping portion 4a. Manipulation of the bending operation knob 4b leads to traction of the wire 18 and curvature of the actively curvable portion 3b. In addition, the operation unit 4 contains various types of boutons that manipulate the endoscope 2. The treatment device insertion port 4c is an opening for communicating with the treatment device channel 16. A procedural device can be inserted into the treatment device channel 16 through the treatment device insertion port 4c.

Universal cable 5 is extended from, for example, the side of the base end of operation unit 4 and a connector 5a is provided to connect to the light source device 6 and the endoscope control device 7. When the connector 5a is connected to the light source device 6 and the endoscope control device 7, the light guide 15 is connected to the light source device 6 and the signal line 14 is connected to the endoscope control device 7.

The light source device 6 supplies illumination light to the light guide 15 of endoscope 2. The light source device 6 includes a white light source that emits white illumination light, and, if necessary, a special light source that emits special light. Examples of special light sources include laser light sources for irradiating stones, light sources of excited light for emitting fluorescent from the subject, and light sources for performing NBI (narrow band light observation).

The endoscope control device 7 transmits a driving signal and power to the imaging element 13. Imaging element 13 captures an optical image of the subject in response to the drive signal and generates an imaging signal. Imaging by the imaging element 13 is sequentially performed in units of frames, for example, an imaging signal according to a moving image of a plurality of frames is generated. The imaging signal is transmitted via the signal line 14 to the endoscope control device 7.

The endoscope control device 7 receives the imaging signal obtained by the imaging element 13, performs functions such as demosaicing, noise correction, color correction, and contrast correction, performs various image processing such as gamma correction, and generates a displayable image signal. Endoscopic control device 7 may combine image signals with various information, such as letter information and guide information. In addition, the endoscope control device 7 may contain various electronics components such as an ASIC (Application Specific Integrated Circuit) including a CPUs (Central Processing Unit), other integrated circuits for specified applications, a FPGA (Field Programmable Gate Array) and the like, to carry out functions of each part by reading and performing a processing program stored in memory devices (or recording media) such as memories. In addition, the endoscope control device 7 may be constituted, at least in part, as a dedicated electronic circuit.

The image signal generated by the endoscope control device 7 is outputted to monitor 8. Monitor 8 is a display device that receives an image signal from the endoscope control device 7 to display the endoscope image.

FIG. 4 is a cross-sectional view showing the apical portion 3*a* of another endoscope 2 containing an arm 24 that is pivotable to change the position, such as direction or orientation, of the treatment device protruding from the treatment device channel 16.

A distal end body 21 (providing a housing for built-in components associated with the endoscope, such as an imaging unit 11, a signal line 14, etc.) is provided on the apical portion 3*a* of the insertion portion 3 and a cylindrical outer member 22 is provided on the outside to encase the distal end body 21 and associated built-in components. The imaging unit 11, the signal line 14, the light guide 15, the treatment device channel 16, the curved frame 17, and the curved wire 18 are located within the interior space formed by the outer member 22. Many parts of the insertion portion 3, including the distal end body 21, the cylindrical outer member 22, the light guide 15, and the treatment device channel 16, are made of materials such as resin that are radiolucent and readily penetrated by X-rays.

Within the outer member 22 is a cavity 23 in communication with the treatment device channel 16. Cavity 23 has an opening Ai on one side of the apical portion 3*a*. An arm 24 is pivotably supported by a support shaft 25 and is disposed in the cavity 23. A wire (not shown) is connected to the treatment device arm 24. When the wire is pulled toward the proximal direction, the arm 24 moves from the standby position (indicated in FIG. 4 by solid lines for the arm 24) to the elevated position (indicated in FIG. 4 by a two-dot chain line for the arm 24) by rotating a base end of the arm about support shaft 25. In a state in which a treatment instrument protrudes from the treatment device channel 16 and contacts the arm 24, when the arm 24 rotates to the elevated position, the distal end portion of the treatment instrument rises and protrudes from the opening 23*a*.

Reusable endoscopes, which are used multiple times, are used to evaluate stone diameters and stricture lengths by comparing on X-ray images the stones and strictures to, for example, the thickness of the insertion portion. In comparison with reusable endoscopes, single-use endoscopes are more difficult to contrast the insertion portion due to the easy penetration of X-rays (electromagnetic waves at wavelengths ranging from 1 to 10 nm) of the resin materials used in most parts, making it difficult to compare the size of the insertion.

Figure 5:
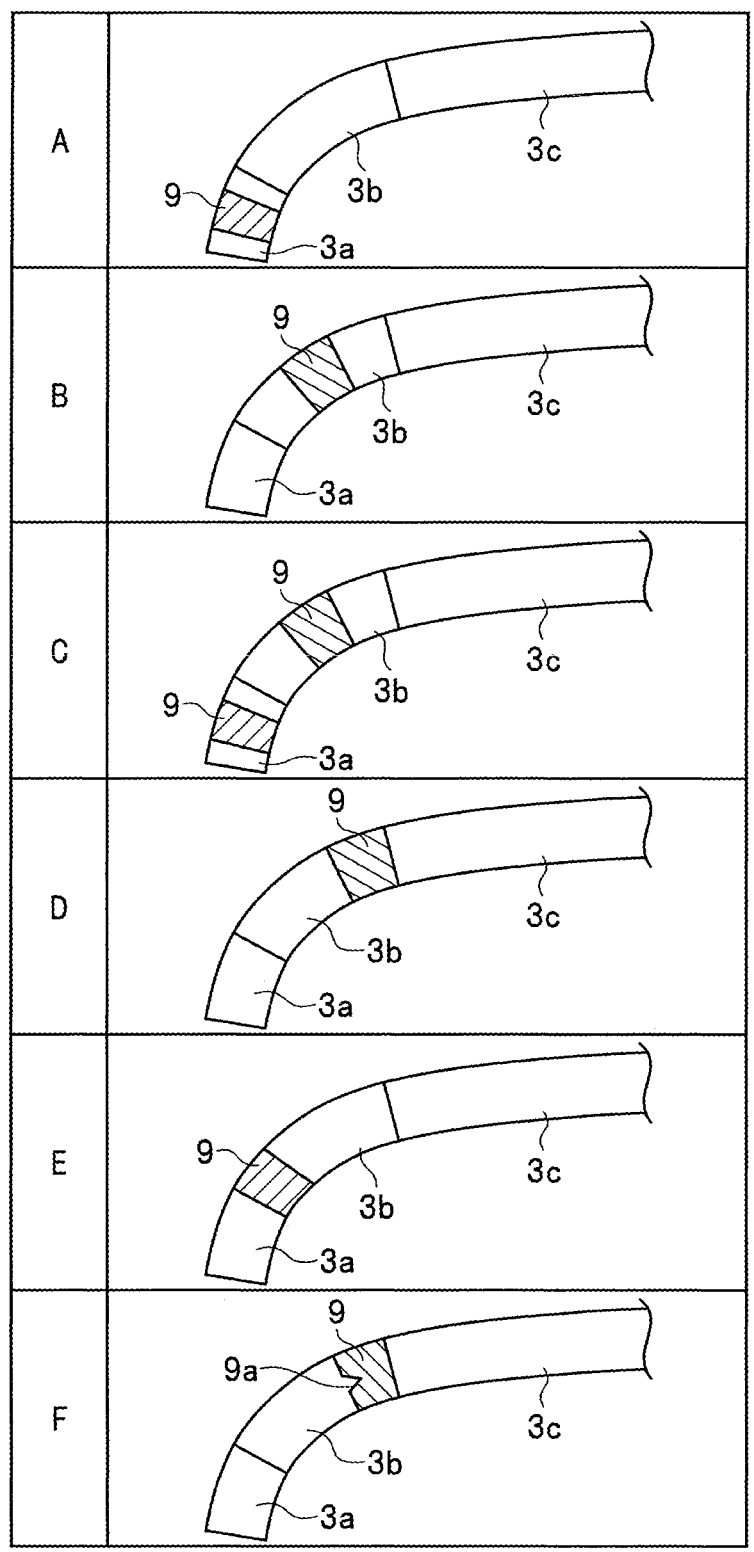
FIG. 5 shows, for the first embodiment, a predetermined position between the proximal end of the actively curvable portion from the tip of the tip configuration portion of the insertion portion is a diagram showing an example of providing a member.

Therefore, a configuration will be described in which, even if many portions of the insertion portion 3 are formed of resin, evaluation of the size becomes possible. FIG. 5 is a diagram showing examples (examples A to F) of providing a radiopaque member 9 at a predetermined position between the proximal end of the actively curvable portion 3*b* and the tip of the apical portion 3*a* of the insertion portion 3. The X-ray transmittance of the radiopaque member 9 is different from the X-ray transmittance of the resin (used to form various portions of the insertion portion 3). Radiopaque member 9 is formed in a predetermined dimension.

In the example shown in FIG. 5, the radiopaque member 9 has a ring-like shape and is less permeable to X-rays than the resin used to form various portions of the insertion portion 3. Radiopaque member 9 is located at one or more locations along the apical portion 3*a* and/or the actively curvable portion 3*b* of insertion portion 3. Radiopaque member 9 is composed of a radiopaque material to provide contrast under X-ray imaging, e.g., metallic rings. Radiopaque member 9 is of a known size and is, for example, 10 mm in diameter for comparison of the size of the measured portion. However, a 5-mm diameter radiopaque member may be added in addition to a 10-mm diameter radiopaque member 9 to allow for more detailed size comparisons.

The following examples are provided: Column A in FIG. 5 shows an example in which a radiopaque member 9 is only located in the apical portion 3*a*; Column B in FIG. 5 shows an example in which a radiopaque member 9 is only located in the actively curvable portion 3*b*; Column C in FIG. 5 shows an example in which a first radiopaque member 9 is located in apical portion 3*a* and a second radiopaque member 9 is located in actively curvable portion 3*b*; Column D in FIG. 5 shows an example in which a radiopaque member 9 is located at the junction between the base-end side of actively curvable portion 3*b* and the flexible tube portion 3*c* (in this example, radiopaque member 9 is composed of a metal ring and may function to reinforce the connection between the actively curvable 3*b* and the flexible tube portion 3*c*); Column E in FIG. 5 shows an example in which a radiopaque member 9 is located at the connection between the apical side of actively curvable portion 3*b* and the apical portion 3*a* (in this example, radiopaque member 9 is composed of a metal ring and may function to reinforce the connection between the actively curvable portion 3*b* and the apical portion 3*a*); and Column F in FIG. 5 shows an example in which a radiopaque member 9 is located at the junction between the base-end side of actively curvable portion 3*b* and the flexible tube portion 3*c*.

In the Column F example, the radiopaque member 9 includes a V-shaped notch 9*a*. The notch 9*a* is a predetermined shape formed in radiopaque member 9 as a mark (indicator) indicating a predetermined dimension of radiopaque member 9. The notch 9*a* should be such that the number of notches or shape of the notch represents a given dimension for the radiopaque member 9. For example, a particular number (such as a single notch) or shape (such as a V-shape) can indicate that the predetermined dimension of the radiopaque member 9 is 10 mm; a different number (such as two notches) or different shape (such as a square notch) can indicate that the predetermined dimension of the radiopaque member 9 is 5 mm; and the like.

Note that the shape of the notch 9a is not limited to a V-shape, but may be in a square shape, or may be in any other arbitrary shape. Also, notch 9a may be applied to any of the radiopaque members 9 described in columns A-E of FIG. 5 or may be applied to the radiopaque members 9 of FIGS. 6-8 and 10 described later.

In order to compare the radiopaque member 9 and the stone, which is a measurement target portion of the subject, it is preferable that the radiopaque member 9 is disposed within a range of 30 cm from the distal end of the apical portion 3a.

Figure 6:
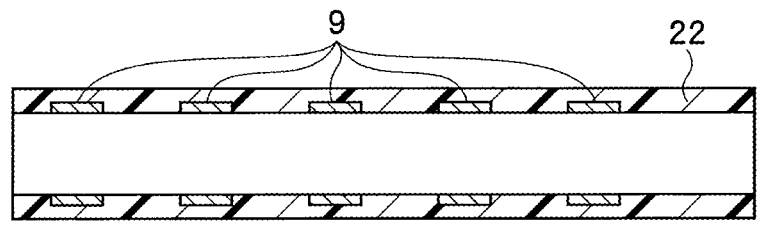
FIG. 6 shows, for the first embodiment, a cross-sectional view showing an example of providing a plurality of members on the inner peripheral side of the outer member.

FIG. 6 is a sectional view showing an example of providing a plurality of radiopaque members 9 on the inner peripheral surface of the outer member 22. The inner surface of the outer member 22 is modified with slots or other depressions and each of the plurality of radiopaque members 9 are positioned in a respective one of the slots. The multiple radiopaque members 9 are, for example, metal rings. Multiple radiopaque members 9 are arranged at predetermined intervals along the longitudinal axis of the insertion portion 3 (hereafter referred to as axially). In the example shown in FIG. 6, for example, five radiopaque members 9 are arranged axially. Here, the outer diameter of radiopaque member 9 is 10 mm, the axial length is 5 mm, and the intervals between the two adjacent radiopaque parts 9 are, for example, 7.5 mm. By doing so, stone size can be compared in 2.5 mm increments.

Figure 7:
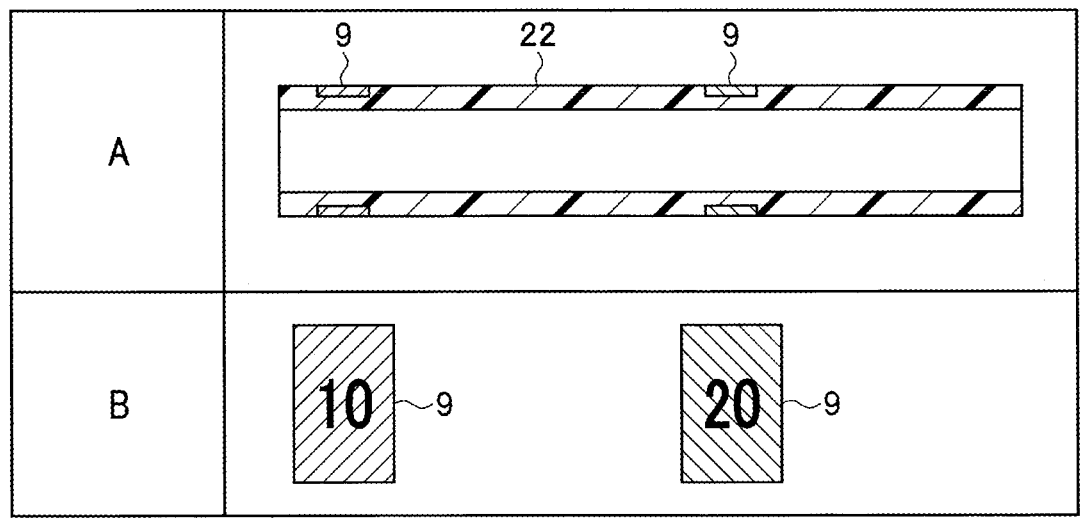
FIG. 7 shows, for the first embodiment above, a cross-sectional view and a lateral view showing an example in which multiple parts are placed on the outer circumferential side of the outer member.

FIG. 7 is a cross-sectional view, side view showing an example of providing a plurality of radiopaque members 9 on the outer peripheral side of the outer member 22. On the surface of the outer peripheral side of the outer member 22, radiopaque members 9 of a plurality of predetermined dimensions are disposed. Radiopaque member 9 coated outside of the outer member 22 can be constituted as, for example, a radiopaque line. A plurality of radiopaque members 9 are arranged at predetermined intervals in the axial direction. In the example shown in FIG. 7, for example, two radiopaque members 9 are arranged in the axial direction. The axial length of radiopaque member 9 is, for example, 5 mm. Note that the intervals between the two radiopaque members 9 may be 10 mm as described above, but the radiopaque members 9 may also include an indicator, such as a numeral or other symbol, that indicates the distance from the tip of the insertion 3, as shown in column B in FIG. 7.

In column A in FIG. 7, the left side is the apical side of insertion portion 3. Indicators in the form of numerals are included in each of the two radiopaque members 9, as shown in column B of FIG. 7. Each indicator is constructed so that it can be identified on the X-ray image, such as by the indicator not being radiopaque. Radiopaque member 9 located on the apical side of insertion portion 3 contains an indicator, such as "10", and radiopaque member 9 located on the basal side contains an indicator such as "20". Each of these numerals provides an indication of the distance from the tip of insertion portion 3, with the number "10" indicating a position of 10 cm from the tip and the number "20" indicating a position of 20 cm from the tip.

Note that when the radiopaque line is placed in a ring-like circumference, the values shown in column B in FIG. 7 overlap with the half-circumferential part of the opposite side of the circumference, so that X-rays are not permeable and indicators cannot be distinguished. Therefore, if an indicator such as a numeral or a letter is provided, a radiopaque line may be made up of a radiopaque component 9 with only half a circumference.

Figure 8:
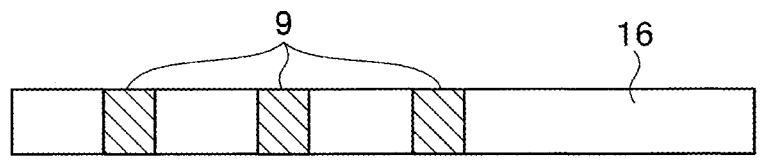
FIG. 8 shows, for the first embodiment above, a lateral view showing an example in which a member is placed in a treatment device channel.

FIG. 8 is a lateral view showing an example in which a radiopaque member 9 is placed in the treatment device channel 16. For example, on the outer peripheral side of the treatment device channel 16, a plurality of radiopaque members 9 are arranged at predetermined intervals in the axial direction. The multiple radiopaque members 9 are metallic rings or other radiopaque structures. In the example shown in FIG. 7, for example, three radiopaque members 9 are arranged in the axial direction. Using the axial length of radiopaque member 9 as, e.g., 5 mm, and the interval between the two adjacent radiopaque members 9 as, e.g. 10 mm, the size of the stone can be compared with the two lengths.

Further, as shown in FIG. 2, a ring-shaped radiopaque member 9 can be located on the outer periphery of the imaging unit 11 and the ring-shaped radiopaque member 9 can be positioned within the body of the apical portion 3a at a position along the axial length of the insertion portion 3. If the diameter of the imaging unit 11 is, e.g. 10 mm or close to 10 mm, the diameter of radiopaque member 9 may be set to 10 mm. Also, if the diameter of imaging unit 11 is, e.g., 5 mm or close to 5 mm, the diameter of radiopaque member 9 may be set to 5 mm.

In addition, the arm 24 shown in FIG. 4 is composed of materials with different radiolucency than resin (specifically, a lower radiolucency than resin). For example, the arm 24 may be composed of metals and formed into sizes and shapes including predetermined dimensions (5 mm, 10 mm, etc.).

Alternatively, the curved frames 17 shown in FIG. 4 are composed of materials with different radiolucency than resin (specifically, lower radiolucency than resin). For example, a curved frame 17 may be composed of metals and formed into sizes and shapes including predetermined dimensions (5 mm, 10 mm, etc.). In this case, one curved frame 17 may have a predetermined dimension and a plurality of curved frames 17 which are continuously provided in the axial direction of the insertion portion 3 may be arranged for each predetermined dimension.

Figure 9:
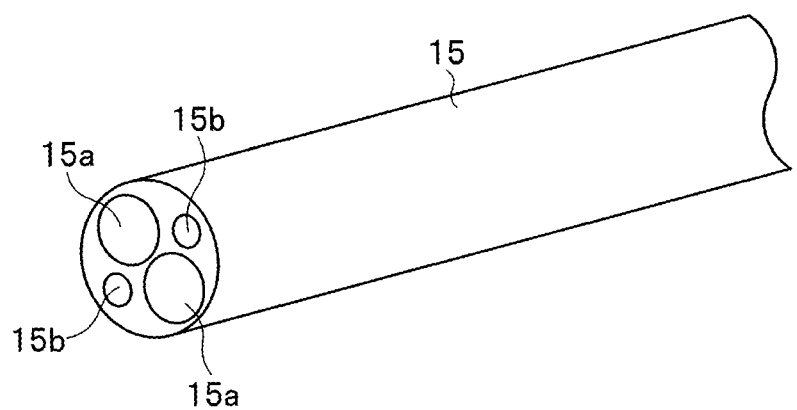
FIG. 9 shows, for the first embodiment above, a perspective view showing an example configuration of a light guide.

FIG. 9 is a perspective view showing an example of the configuration of the light guide 15. Light guide 15 includes a first optical fiber 15a having a relatively large diameter, and a second optical fiber 15b having a relatively small diameter. The outer diameter of the first optical fiber 15a is, for example, 1 mm, and the outer diameter of the second optical fiber 15b is, for example, 0.3 mm. In the example shown in FIG. 9, the light guide 15 is composed of two first optical fibers 15a, and two second optical fibers 15b.

Figure 10:
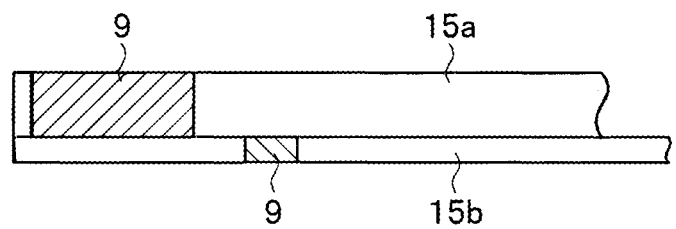
FIG. 10 shows, for the first embodiment, a side view showing an example of a member provided in the optical fiber of the two types of diameters.

FIG. 10 is a side view showing an example of a radiopaque member 9 provided in the optical fibers 15a, 15b having the two different diameters. A radiopaque member 9 on the outer periphery of at least one first optical fiber 15a has an outer diameter of 1 mm and a length of 10 mm and, for example, is formed by a metal coating. A radiopaque member 9 on the outer periphery of at least one second optical fiber 15b has an outer diameter of 0.3-mm and a length of 5-mm-long and, for example, is formed by a metal coating. At this time, the radiopaque member 9 provided in the first optical fiber 15a and the radiopaque member 9 provided in the second optical fiber 15b are arranged at different positions in the axial direction so that the axial position of the respective radiopaque members 9 do not overlap (i.e., so as to appear as separate bodies on the X-ray image).

Alternatively, instead of forming radiopaque members 9 by metallic coating, radiopaque members 9 may be formed by X-ray opaque materials, such as barium, or X-ray fluorescent materials, etc.

The various configurations disclosed herein allow the operator to identify four lengths, i.e., 0.3 mm, 1 mm, 5 mm, and 10 mm, under radiographic observation, and compare these lengths with stones to provide a fine assessment of stone size. Incorporating radiopaque members 9 of different sizes and positioned at different axial locations allow for different combinations of lengths to be identified under radiographic observation.

According to such a first embodiments, the size of radiopaque member 9 can be clearly confirmed on the X-ray image by providing a radiopaque member 9 with different radiolucency from the resin that constitutes many parts of the insertion portion 3, and on the X-ray image, it is possible to evaluate the size of the stone by comparing the stone with the size and or separations distance of the radiopaque member(s) 9.

Second Embodiment

FIGS. 11 to 22 show a second embodiment of the present invention. In the second embodiment, the different points are mainly explained and, in general, the explanation is omitted for similar parts having the same reference numerals as in the first embodiments.

Figure 11:
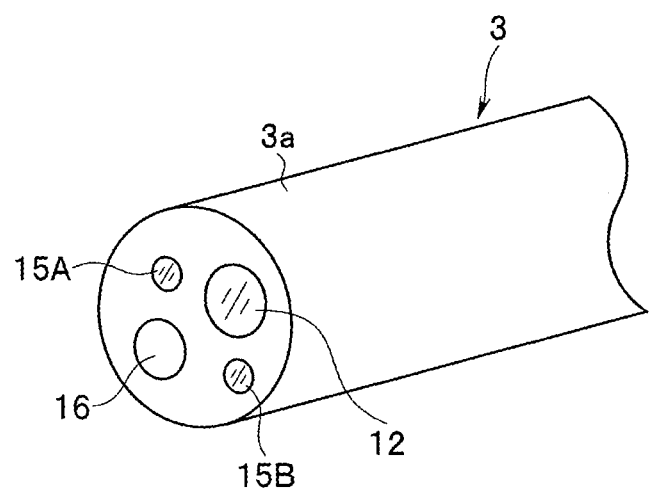
FIG. 11 is a perspective view showing a distal end configuration portion of an endoscope in the optical probe system of the first configuration example in a second embodiment of the present invention.

FIGS. 11 to 16 show an example of the first configuration of the second embodiment, and FIG. 11 is a perspective view showing the apical portion 3a of endoscope 2 in the optical probe system of the first configuration example. The optical probe system of the first configuration example is illustrated as a measurement system with laser light and has endoscope 2 as an optical probe. As shown in FIG. 11, the endoscope 2 includes an objective optical system 12 and a treatment device channel 16, with a first light guide 15A and a second light guide 15B.

Figure 12:
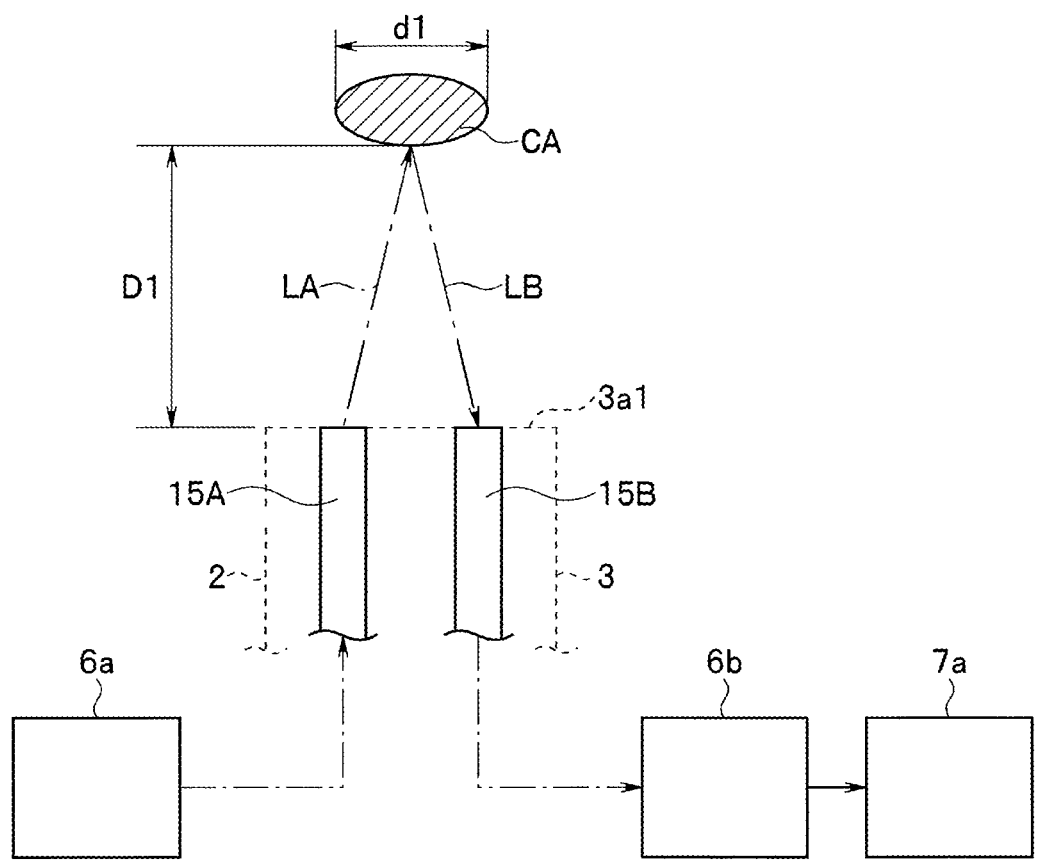
FIG. 12 illustrates an optical probe system of the first example of the second embodiment above, illustrating how the laser light is delivered from the first light guide to the stone and the reflected light from the stone is received by the second light guide.
Figure 13:
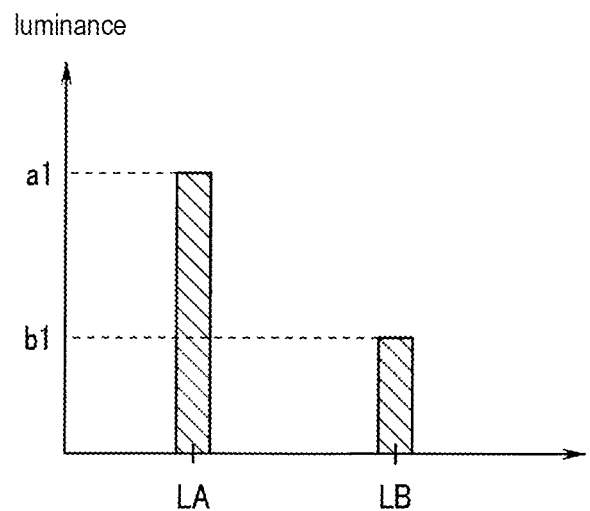
FIG. 13 shows, for the first configuration example of the second embodiment, the emitted light of the laser and the reflected light received is a bar graph showing an example of the brightness.

FIG. 12 shows a light probe system in the first configuration, in which laser light is delivered from the first light guide 15A to the stone CA and reflected light from the stone CA is received by the second light guide 15B. FIG. 13, in the first configuration example, is a bar graph showing an example of the brightness of the emitted light LA of the laser and of the received reflected light LB.

As shown in FIG. 12, the light probe system includes a laser-emitting light source 6a, an endoscope 2, a sensor 6b, and an analyzer 7a. For example, the light source 6a and sensor 6b is provided in the light source device 6, and the analyzer 7a is provided in the endoscope control device 7.

As shown in FIG. 12, the light source 6a emits a laser beam having a predetermined luminance a1. The first light guide 15A transmits the laser beam emitted from the light source 6a to the distal end by receiving light at the proximal end. The first light guiding 15A delivers the transmitted laser light as an emitted light LA to a stone CA of diameter d1 position at an unknown distance D1 from the distal end surface 3a1 of insertion portion 3. The emitted light LA is reflected by the stone CA and reflected light LB is generated as the return light. The second light guide 15B receives the reflected light LB and transmits to the light source device 6. Reflected light LB is measured brightness b1 by the sensor 6b provided in the light source device 6. Analyzer 7a acquires the luminance a1 of the emitted light LA and the brightness b1 and the reflected light LB (see FIG. 13) from the light source device 6 and calculates the luminance ratio b1/a1.

Figure 14:
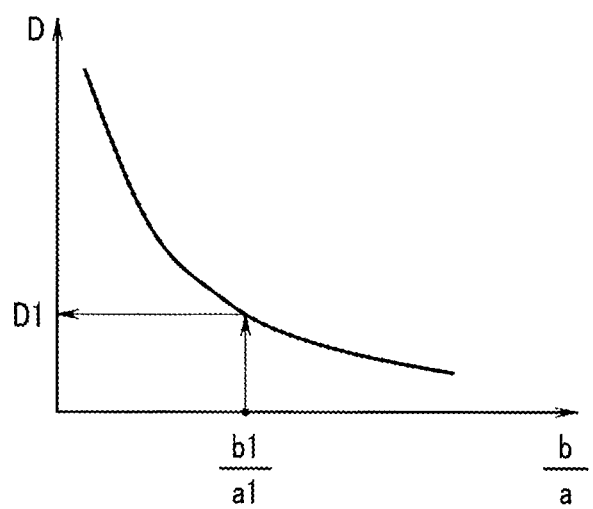
FIG. 14 shows, for the first example of the second embodiment above, a graph showing the relationship between the ratio of the brightness of reflected light to the brightness of the configuration light of the laser and the distance from the apical surface of the insertion to the stone.

FIG. 14 is a graph showing, in the first configuration example, the relationship between the ratio (b/a) of the brightness (b) of reflected light to the luminance (a) of the emission light of the laser and the distance D from the distal end surface 3a1 of insertion portion 3 to the stone CA. In general, the luminance ratio (b/a) is correlated with the distance D: the greater the distance D, the luminance ratio (b/a) is reduced. Therefore, as in FIG. 14, a graph plotting the correlation between the luminance ratio (b/a) (on the horizontal axis) and the distance D (on the vertical axis) can be obtained by measuring in advance. Data corresponding to the graph in FIG. 14 are pre-determined and stored in the memory in analyzer 7a. Based on the luminance ratio (b1/a1) calculated from the measurement results of FIGS. 12 and 13, analyzer 7a, can calculate the distance D1 corresponding to the luminance ratio (b1/a1) by referencing the correlation graph of FIG. 14.

Figure 15:
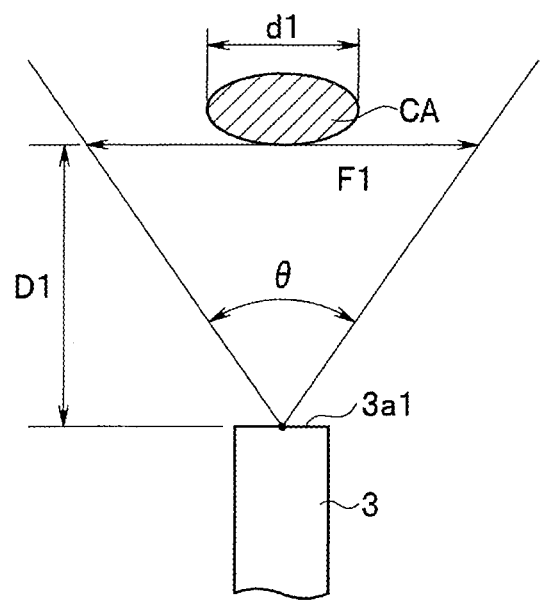
FIG. 15 shows, for the first configuration example of the second embodiment, a diagram for explaining a positional relationship when imaging a stone.

FIG. 15 is a view for explaining a positional relationship when imaging a stone CA in the first configuration example. The viewing angle θ of the objective optical system 12 of endoscope 2 is known because it is predetermined by the design. Analyzer 7a calculates the width F1 of the imaging range at distance D1 to the stone CA measured by irradiating laser light, e.g., as in Formula 1.

$$F1 = 2 \times D1 \times \tan(\theta/2) \qquad \text{[Mathematical formula 1]}$$

Figure 16:
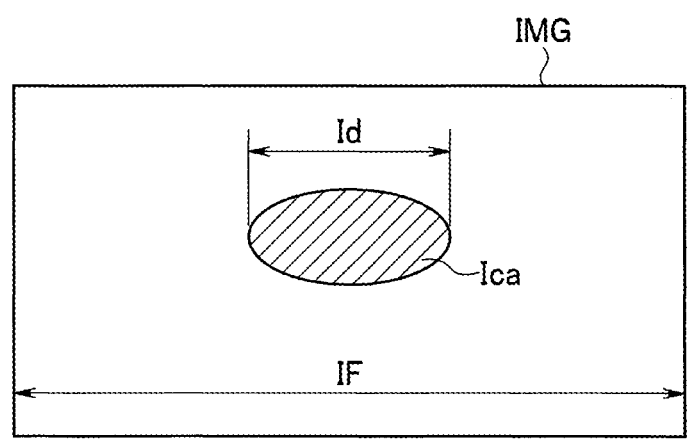
FIG. 16 illustrates, for the first example of the second embodiment, an example of an endoscopic image in which optical imaging of an object containing a stone has been imaged into the imaged region of the imager.

FIG. 16 shows an example of an endoscopic image IMG in which, in the first configuration example, an optical image of the subject containing the stone CA located in the imaged region of the imaging element 13 and acquired.

The size of the endoscopic image IMG, e.g., the width of the endoscopic image IMG, is taken as IF, the size of the image of the stone CA is taken as Ica, and the measurement object part of the subject, e.g., the diameter of the image Ica, is taken as Id. From FIGS. 15 and 16, there is a relationship shown as Formula 2.

$$d1/F1 = Id/IF \qquad \text{[Mathematical formula 2]}$$

From Formula 2, analyzer 7a calculates the actual diameter d1 of the stone CA at distance D1 as in Formula 3.

$$d1 = F1 \times (Id/IF) \qquad \text{[Mathematical formula 3]}$$

Accordingly, in the first configuration example, the actual diameter d1 of the stone CA can be obtained from the endoscopic image by obtaining the distance D1 to the stone CA based on the intensity ratio of the laser emission light LA and reflected light LB.

Figure 17:
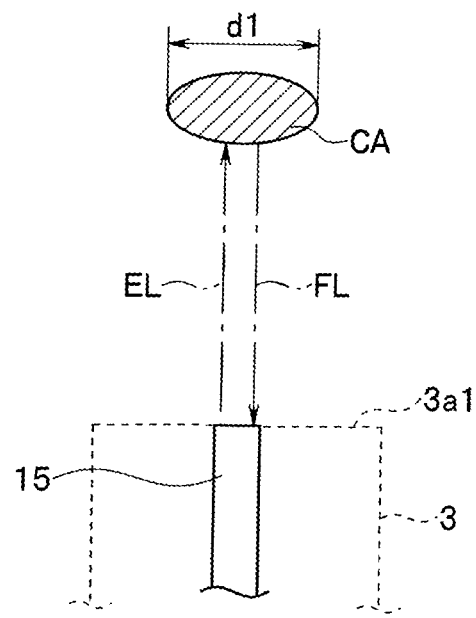
FIG. 17 shows, for the optical probe system of the second configuration example of the second embodiment, a diagram showing a state of receiving fluorescent by irradiating excitation light to the stone.
Figure 18:
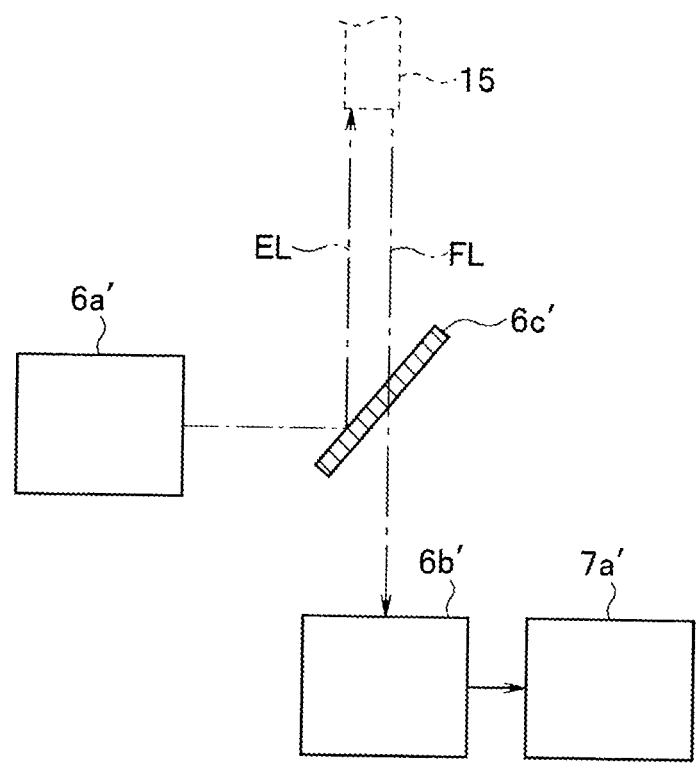
FIG. 18 shows, for the second example of the second example above, a diagram showing the organization of the optical probe system that emits excited light from the light source and detects the fluorescent transmitted by the light guide by the sensor.
Figure 19:
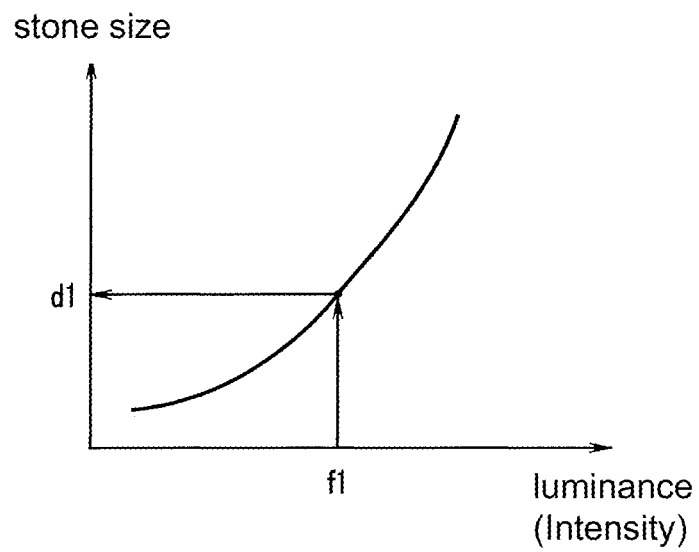
FIG. 19 shows, for the second example of the second example above, a graph showing an example of the relationship between the luminance of fluorescent detected by the sensor and the size of the stone.

FIGS. 17 to 19 show a second configuration example of the second embodiment. FIG. 17 is a diagram showing a second configuration example, in the optical probe system of the second configuration example, by irradiating the excitation light EL to the stone CA to receive the fluorescent light FL. FIG. 18 shows, in a second configuration example, the organization of an optical probe system that emits excited light EL from the light source 6a' and detects fluorescent light FL transmitted by light guide 15 by sensor 6b'. The optical probe system of the second configuration example is configured as a fluorescence measurement system, as shown in FIG. 18, and includes a light source 6a' for emitting excitation light EL, a sensor 6b', a half mirror 6c', and an analyzer 7a'.

In the following, light guide 15 of endoscope 2 is used for transmission of excited light EL and fluorescent light FL and the illustrating examples include light sources 6a', half-mirror 6c', and sensor 6b' that are provided in the light source device 6 and analyzer 7a' is provided in the endoscope control device 7, but embodiments are not limited to such configurations.

That is, in the second configuration example, the size of the stone CA can be detected without obtaining endoscopic images. For this reason, instead of endoscope 2, a light probe with a light guide may be used to detect the size of the stone CA. In this case, an optical probe system may be constructed separately from the endoscope 2, the light source device 6, and the endoscope control device 7. The optical probe may be inserted through the treatment device channel 16 of the endoscope 2

When the light source 6a 'emits excitation light EL, the excitation light EL is reflected by the half mirror 6c', it is incident on the proximal end of the light guide 15. Excited light EL transmitted by light guide 15 is delivered from the tip of light guide 15 to the stone CA, as shown in FIG. 17. Stone CA is excited when subjected to excitation light EL and emits fluorescent light FL. Fluorescent light FL emitted from the stone CA is incident on the tip of the light guide 15, transmitted by the light guide 15, and exits from the base end of the light guide 15. Thus, in the second configuration example, a single light guide 15 is sufficient.

Fluorescent light FL exiting from the base end of the light guide 15 passes through the half-mirror 6c' and brightness f1 is measured by the sensor 6b'. Note that if not only fluorescent light FL but also excited light EL are included in the return light from the stone CA, an excited light cut filter may be placed on the optical path between the half-mirror 6c' and sensor 6b'. Further, when using the half mirror 6c', the excitation light EL emitted from the light source 6a' is partially reflected to the light guide 15 side and a portion of the excitation light EL will be transmitted through the half mirror 6c', in which case wasting of light emission occurs. Furthermore, when using the half mirror 6c', the fluorescent light FL transmitted by the light guide 15 is partially transmitted to the sensor 6b' side, but another portion of the fluorescent light FL will be reflected to the light source 6a' side, hence the amount of light of the fluorescent light FL received by the sensor 6b' is reduced, so that the sensitivity of the sensor 6b' is reduced. In general, the wavelengths are different from excited light EL and fluorescent light FL. Therefore, instead of half-mirror 6c', a dichroic mirror or the like may be used that reflects light in the wavelength range of the excited light EL and passes light in the wavelength range of the fluorescent light FL.

FIG. 19 is a graph showing an example of the relationship between luminance of fluorescent light FL detected by sensor 6b' and size of stone CA in a second configuration example. There is a correlation between the luminance (Intensity) of fluorescent light FL that is excited and emitted by stone CA and the size of stone CA. Pre-determination of this correlation provides a graph such as shown in FIG. 19. Therefore, by calculating the graph of FIG. 19 based on the luminance f1 of the fluorescent light FL obtained from actual measurements, it is possible to calculate the size d1 of the stone CA.

Accordingly, in the second configuration example, the size of the stone CA can be acquired by measuring the brightness of the fluorescent light FL generated by irradiating the stone CA with the excitation light EL.

Figure 20:
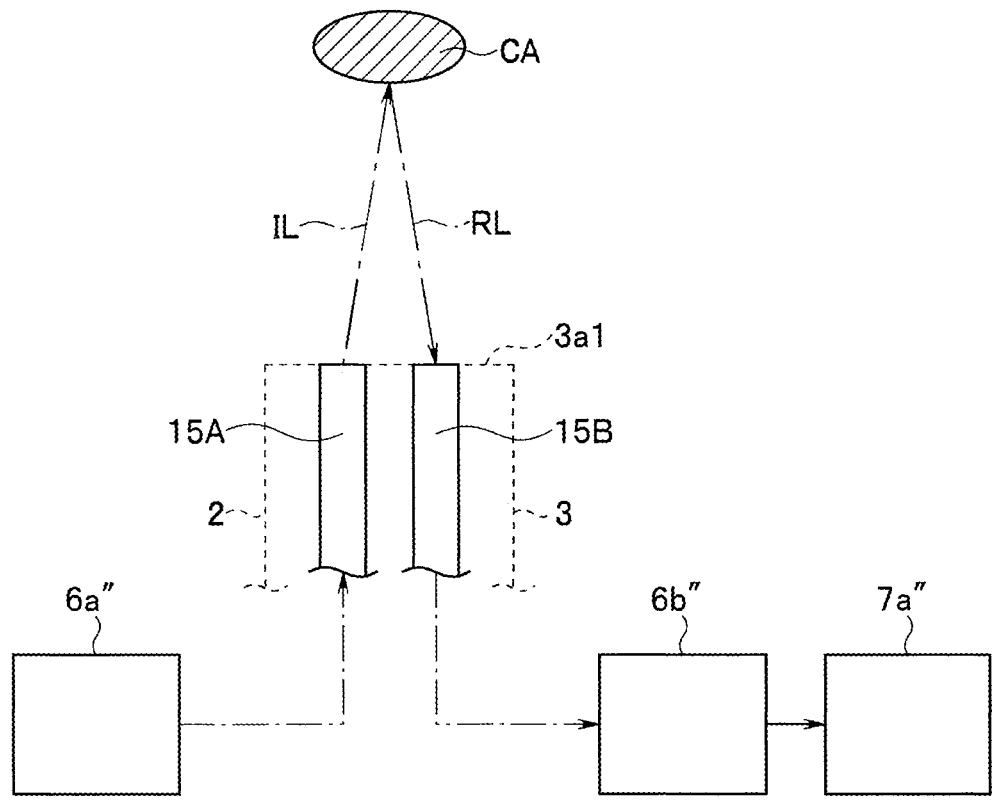
FIG. 20 is an illustration showing the optical probe system in the third configuration example of the second embodiment above.
Figure 21:
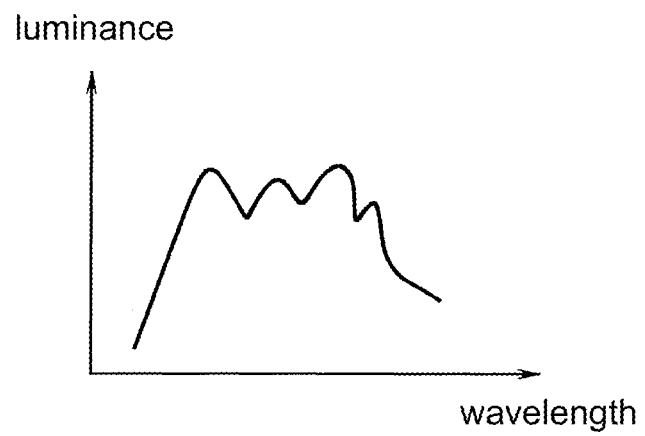
FIG. 21 shows, for the third configuration example of the second embodiments above, a graph showing an example of the brightness distribution relative to the wavelength obtained by spectroscopically analyzing the reflected light from the stone.

FIG. 20 and FIG. 21 show the third configuration example of the second embodiment. FIG. 20 is a figure showing the optical probe system in the third configuration example. FIG. 21 is a graph showing examples of brightness distributions for wavelengths obtained by spectroscopic analysis of reflected optical light RLs from the stone CA in a third configuration example.

The optical probe system of the third configuration example is constructed as a stone analysis system and includes a light source 6a'', an endoscope 2, a sensor 6b'', and an analyzer 7a'', as shown in FIG. 20. For example, the light source 6a'' and sensor 6b'' are provided in the light source device 6, and the analyzer 7a'' is provided in the endoscope control device 7. However, the embodiment is not limited to light source device 6 and endoscope control device 7, but rather a separate stone analysis system may be provided. In addition, the embodiment is not limited to endoscope 2, but rather an optical probe may be used in the same manner as the endoscope 2 in the configuration example.

Light source 6a'' emits illumination light IL including light of a plurality of wavelengths, such as white light, for example. Endoscope 2 of the third configuration embodiment, similarly to the configuration shown in FIG. 11, comprises a first light guide 15A and a second light guide 15B. The illuminated IL emitted from the light source 6a'' is transmitted by the first light guide 15A and delivered from the tip of the first light guide 15A to the stone CA. Reflected optical light RL from stone CA irradiated with illuminated light IL enter the tis of the second light guide 15B and is transmitted by the second light guide 15B. Reflected light RL transmitted by the second light guide 15B exits from the proximal end of the second light guide 15B and is incident on the sensor 6b''.

As shown in FIG. 21, sensor 6b'' is a sensor for spectroscopic analysis to measure the brightness of the reflected light RL for each wavelength. Spectroscopic analysis results with sensor 6b'' are sent to analyzer 7a''. Analyzer 7a'' identifies the type of stone CA (e.g., cholesterol-based stones, mixed stones, dye stones, etc.) by comparing the wavelength-luminance value of reflected light RL acquired as a result of spectroscopic analysis from sensor 6b'' with the wavelength-luminance value of known stone CA stored in the memory within analyzer 7a''. The type of stone identified by analyzer 7a'' is displayed with the endoscopic image, e.g. in monitor 8.

By looking at monitor 8 and checking the type of stone identified, the surgeon can choose what type of fracture method to crush the stone CA.

Accordingly, in the third configuration example, the surgeon can assist in choosing the method of fracture of the stone CA.

Figure 22:
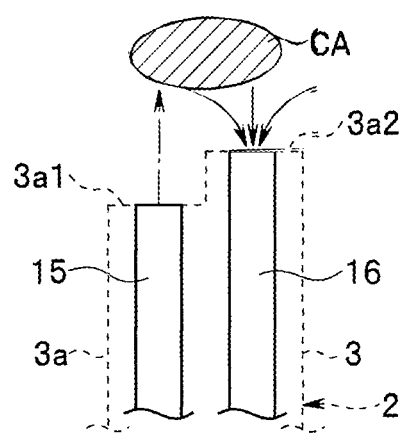
FIG. 22 is a diagram showing an insertion portion of an endoscope in the optical probe system of the fourth configuration example of the second embodiment described above.

FIG. 22 is a view showing an insertion portion 3 of the endoscope 2 in the optical probe system of the fourth configuration example of the second embodiment. The optical probe system of the fourth configuration example includes, for example, an endoscope 2 as an optical probe. However, the optical probe without imaging function may be used instead of the endoscope 2.

Endoscope 2 (or optical probe) has an aspiration channel. Herein, the treatment device channel 16 serves as an aspiration channel, but it may be provided with an aspiration channel separately from the treatment device channel 16. Laser light transmitted by the light guide 15 functioning as a laser light guide is irradiated from the tip of the light guide 15 disposed on the distal end surface 3a1 of the insertion portion 3 and is incident to the stone CA. The tip of insertion portion 3 has a protruding portion 3a2 that protrudes more anteriorly than the distal end surface 3a1. An opening of the treatment device channel 16, which can also serve as a suction channel, is disposed in the protruding portion 3a2.

Because stone CA is movable, it may be difficult to adequately deliver laser light to stone CA, or it may be difficult to retrieve stone CA. Therefore, in the fourth configuration example, use of the following methods can more reliably crush and retrieve the stone CA. To begin with, the stone CA is fixed to the opening of the treatment device channel 16 by carrying out suction from the treatment device channel 16 serving as a suction channel. Once fixed to the opening of the treatment device channel 16, stone CA does not migrate and is fixed at the protruding shape 3$a$2 anterior to the distal end surface 3$a$1 and irradiation of laser light from the tip of the light guide 15 can reliably crush the stone CA. Thereafter, fragmented and morcellated stone CAs are recovered intact using suction applied via the treatment device channel 16.

When stone CA is an organic calculus, a part of stone CA melts when irradiated by laser light. Therefore, when an optical probe is used, it is also possible to use a method of recovering the stone CA that includes bringing the molten stone CA into contact with the optical probe, and then the molten portion is cooled and solidified and then the optical probe is withdrawn.

At this time, a specific method of bringing the molten stone CA into contact with the optical probe is, for example, the following. In a first method, laser light is applied to melt the stone CA, and the tip of the optical probe is caused to approach to the stone CA and to contact the stone CA with the tip of the optical probe. In a second method, the stone CA is melted by irradiating laser light and crushing the stone CA, suction is carried out using suction applied via the treatment device channel 16, and the stone CA is caused to contact the opening of the treatment device channel 16. In a third method, aspiration is performed using suctioning of fluid via the treatment device channel 16 to contact the stone CA with the opening of the suction channel, and, while contact between the stone CA and the insertion portion 3 maintained, laser light is applied to melt the stone CA which then solidifies with solidified portion affixed to the insertion portion 3. By adopting these methods, large stone CAs that are difficult to pass through the treatment device channel 161 can also be reliably retrieved.

According to such a second embodiments, it is also possible to evaluate the size of the stone CA using the measuring part in an optical probe system using light such as laser light, excited light, etc. Spectroscopic analysis can also identify the type of stone CA. In addition, aspiration of the stone CA using suctioning of fluid via the treatment device channel 16 ensures that the stone CA can be crushed. And, the stone CA which is fused by the irradiation of the laser light is solidified by contacting the optical probe, and the stone CA can be reliably recovered.

It should be noted that the present invention is not limited to the embodiments described above as they are, and components may be modified and embodied without departing from the scope of the present invention at the stage of implementation. In addition, various aspects of the invention can be formed by appropriately combining a plurality of constituent elements disclosed in the above embodiment. For example, some components may be deleted from all components shown in the embodiments. In addition, components across different embodiments may be combined accordingly. Thus, it is not surprising that a variety of deformations and applications can be made within a range that does not deviate from the intent of the invention.

What is claimed is:

1. An endoscope, comprising:
   an insertion portion including an apical portion, an actively curvable portion positioned at a base-end of the apical portion, and a treatment device channel extending along a longitudinal axis of the insertion portion;
   an imaging unit; and
   one or more radiopaque members,
   wherein the apical portion and the actively curvable portion are formed of a resin,
   wherein the one or more radiopaque members have a first radiolucency, the resin has a second radiolucency, and the first radiolucency differs from second radiolucency,
   wherein the one or more radiopaque members are located in the apical portion or the actively curvable portion,
   wherein the one or more radiopaque members (i) are located on a surface of the apical portion or the actively curvable portion or (ii) are encased within or embedded within the resin forming the apical portion or the actively curvable portion, and
   wherein the one or more radiopaque members has an indicator corresponding to a dimension of the one or more radiopaque members.

2. The endoscope according to claim 1, wherein the one or more radiopaque members is located on the surface of the apical portion.

3. The endoscope according to claim 1, wherein the one or more radiopaque members is located on the surface of the actively curvable portion.

4. The endoscope according to claim 1, wherein the one or more radiopaque members is located within a range of 30 cm from a distal end of the apical portion.

5. The endoscope according to claim 1, wherein said indicator is a shape formed in the one or more radiopaque members.

6. The endoscope according to claim 5, wherein the shape is a notch.

7. The endoscope according to claim 1, wherein the one or more radiopaque members are located on the surface of the apical portion or the actively curvable portion, and
   wherein the one or more radiopaque members are coated on the surface of the apical portion or the surface of the actively curvable portion.

8. The endoscope according to claim 1, wherein the one or more radiopaque members are embedded within the resin forming the apical portion of the insertion portion.

9. The endoscope according to claim 1, wherein the apical portion includes an outer member with an interior space defining a cavity,
   wherein a first end of the cavity is in communication with the treatment device channel within the insertion portion,
   wherein an opening in a portion of the outer member is in communication with the cavity,
   wherein a pivoting arm is disposed in the cavity,
   wherein the pivoting arm is operable between a standby position and an elevated position, and
   wherein, in the standby position, the pivoting arm is within the cavity and, in the elevated position, the pivoting arm extends through the opening in the portion of the outer member.

10. The endoscope according to claim 9, wherein the elevated position of the arm is configured to direct a distal end portion of a treatment instrument protruding from the treatment device channel to protrude from the opening in the portion of the outer member.

11. The endoscope according to claim 1, wherein the one or more radiopaque members are embedded within the resin forming the actively curvable portion of the insertion portion.

12. The endoscope according to claim 1, wherein the one or more radiopaque members are encased within the resin forming the apical portion of the insertion portion or the actively curvable portion of the insertion portion.

13. The endoscope according to claim 1, wherein the one or more radiopaque members are encased within the resin forming the actively curvable portion of the insertion portion.

\* \* \* \* \*